United States Patent
Metz-Stavenhagen et al.

[11] Patent Number: 6,001,098
[45] Date of Patent: *Dec. 14, 1999

[54] CONNECTING ELEMENT FOR SPINAL STABILIZING SYSTEM

[75] Inventors: Peter Metz-Stavenhagen; Bernd Robioneck, both of New York, N.Y.

[73] Assignee: Howmedica GmbH, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/783,940

[22] Filed: Jan. 17, 1997

[51] Int. Cl.⁶ ........................................ A61F 5/04
[52] U.S. Cl. .................. 606/61; 606/60; 606/72
[58] Field of Search ................. 606/54, 60, 61, 606/72, 73, 64, 70, 71; 623/17

[56] References Cited

U.S. PATENT DOCUMENTS

| | | |
|---|---|---|
| 4,773,402 | 9/1988 | Asher et al. . |
| 4,805,602 | 2/1989 | Funo et al. . |
| 5,002,542 | 3/1991 | Frigg .......................................... 606/61 |
| 5,261,909 | 11/1993 | Sutterlin et al. . |
| 5,306,275 | 4/1994 | Bryan ......................................... 606/73 |
| 5,611,800 | 3/1997 | Davis et al. ............................... 606/61 |
| 5,634,925 | 6/1997 | Urboniski .................................. 606/61 |
| 5,643,259 | 7/1997 | Sasso et al. ................................ 606/61 |
| 5,643,264 | 7/1997 | Sherman et al. ........................... 606/61 |
| 5,741,254 | 4/1998 | Henry et al. ............................... 606/61 |
| 5,746,741 | 5/1998 | Kraus et al. ............................... 606/61 |

FOREIGN PATENT DOCUMENTS

| | | |
|---|---|---|
| 9409123U | 6/1994 | Germany . |
| WO 96/28104 | 9/1996 | WIPO . |

*Primary Examiner*—Mickey Yu
*Assistant Examiner*—Bruce E. Snow
*Attorney, Agent, or Firm*—Lerner, David, Littenberg, Krumholz & Mentlik, LLP

[57] ABSTRACT

The invention relates to a connecting element for connecting a screw in the spine with a stabilizing rod, the connecting element being easily and quickly securable. The connecting element includes a receiving section which receives the stabilizing rod and which is part of a tension member having a threaded shank. A sleeve is arranged around the receiving section and can slide parallel to the shank axis. In the wall of the sleeve, two openings are present for positioning the rod. The connecting element further includes a nut which can be screwed onto the shank in order to fix the head of the pedicle screw at the sleeve. This connecting element has the advantage that by a single securing process (i.e., the tightening of the nut) the rod can be fixed in the receptacle of the tension member and the connecting element can be secured at the screw head. Preferably, the receptacle for the rod and the recesses of the sleeve are formed so that an opening is formed which extends transversely through the sleeve and the tension member, with the rod being fixable in that opening by tightening the nut.

11 Claims, 4 Drawing Sheets

CONNECTING ELEMENT FOR SPINAL STABILIZING SYSTEM

BACKGROUND OF THE INVENTION

The invention relates to a connecting element for fixing a rod at a pedicle screw or the like for a stabilizing system for a human spine, the connecting element having a first section for receiving the pedicle screw and a second section for receiving and fixing by clamping a rod passed therethrough.

Stabilizing systems for the human spine usually comprise rods which are dorsally secured at the spine with pedicle, sacral or iliac screws for distraction or compression of the spine or are secured with hooks grasping around the transverse processes of the vertebrae. For connecting the screws and the hooks with the rod, connecting elements are utilized. For instance, connecting elements are known, wherein a first section for receiving a pedicle screw or the like is formed as an elongated hole being led onto the head of the screw and secured with a nut. A second section for receiving the rod comprises a conically formed opening into which the rod is put and fixed by a screw which presses against the rod from the top with the end of the shank.

A disadvantage of these known connecting elements is that two securing means have to be operated in order to connect the rod with the screws inserted into the spine, namely the nut for securing the connecting elements at a screw in the spine and the screw for fixing the rod in the receiving opening of the connecting elements.

OBJECTS OF THE INVENTION

An object of the invention is to provide a connecting element for connecting a screw in the spine with a stabilizing rod, the element being easily and quickly securable.

SUMMARY OF THE INVENTION

The connecting element according to the invention comprises a receiving section (i.e. receptable) which receives the stabilizing rod and which is part of a tension member having a threaded shank. A sleeve having a through-opening for the shank is arranged around the receiving section and can slide parallel to the shank axis. In the walls of the sleeve, two circular openings located opposite each other (or recesses having a C-shape with the closed part of the shape being located near the shank) are present for positioning the rod. The connecting element further comprises a nut which can be screwed onto the shank in order to fix the head of the pedicle screw (or of a similar screw which is to be screwed into the spine), at the sleeve. Simultaneously with the fixation of the screw, the sleeve has been slidingly displaced towards the end of the tension member so far that the rod inserted into the receptacle is secured within the receptacle and the openings or the recesses of the sleeve by clamping.

This connecting element has the advantage that the rod can be fixed in the receptacle of the tension member and the connecting element can be secured at the screw head by a single securing process, namely the tightening of the nut.

The second section which receives the rod can comprise a circular opening for receiving the rod. Preferably, the center thereof lies on the longitudinal axis of the connecting element. Thereby, the connecting element or at least a part of the rod which usually is flexible around the longitudinal axis of the connecting element during fixation can be turned more easily.

Alternatively, the second section can comprise a recess open transversely to the shank axis. This can be a longitudinal recess with a semi-circular end. This form of the receptacle has the advantage that the rod can be put in and does not have to be pushed through the opening; and this can save time when using a longer rod which is to be secured at several connecting elements.

The recesses of the sleeve can be open towards the free end thereof, whereby a sliding onto the second section from the side facing the shank is possible if a rod is located in the second section. Preferably, the receptacle for the rod and the recesses of the sleeve are formed so that an opening is formed which extends transversely through sleeve and tension member, with the rod being fixed by clamping in the opening.

The sleeve can comprise teeth around the throughgoing opening of the shank for engaging with teeth of the pedicle screw head. Especially if such teeth are provided, it is advantageous if the sleeve is round in cross section and turnable on the tension member around the shank axis thereof.

The sleeve can be slidable onto the shank of the tension member, whereby the sleeve through-opening for the shank is smaller than the transverse dimensions of the second section so that the sleeve upon a sliding in the direction of the second section finally strikes it if no rod is inserted into the receptacle. Therefore, the second section preferably can comprise an inwardly inclined region within the transition region towards the shank, the inclined region constituting a stop face for the corresponding inner surface of the sleeve.

For engaging with an opening or recess in the pedicle screw head, the nut can have a collar.

DETAILED DESCRIPTION OF THE PREFERRED EMBODIMENTS

Figure 1:
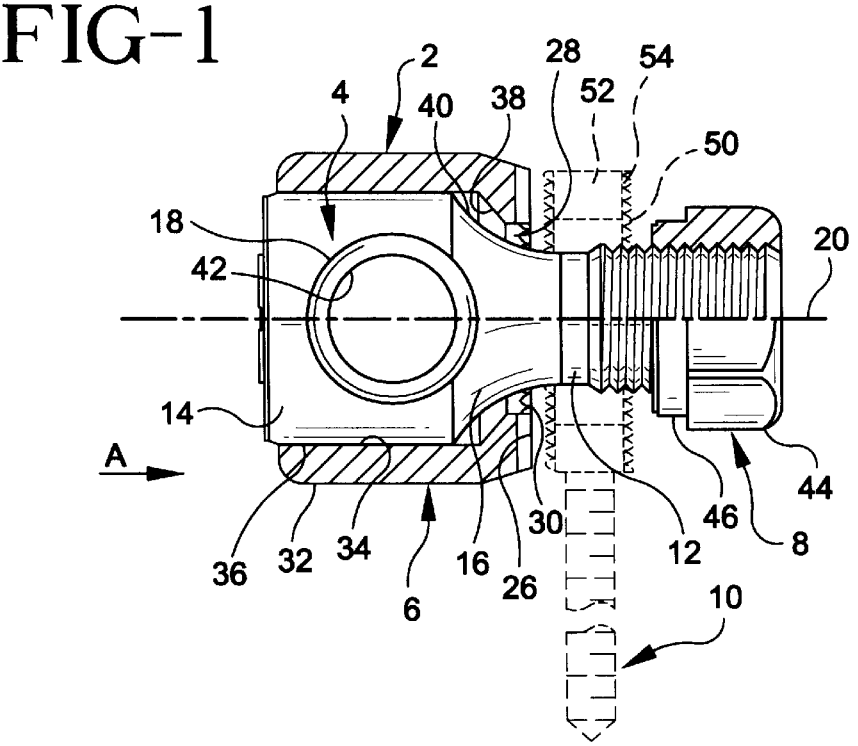
FIG. 1 shows a connecting element 2 in elevational view, partly in sectional view, and schematically a pedicle screw.

FIG. 1 shows a connecting element 2 which includes a tension member 4, a sleeve 6 and a nut 8. Furthermore, FIG. 1 shows schematically a pedicle screw 10 in phantom at which the connecting element 2 is secured.

Figure 2:
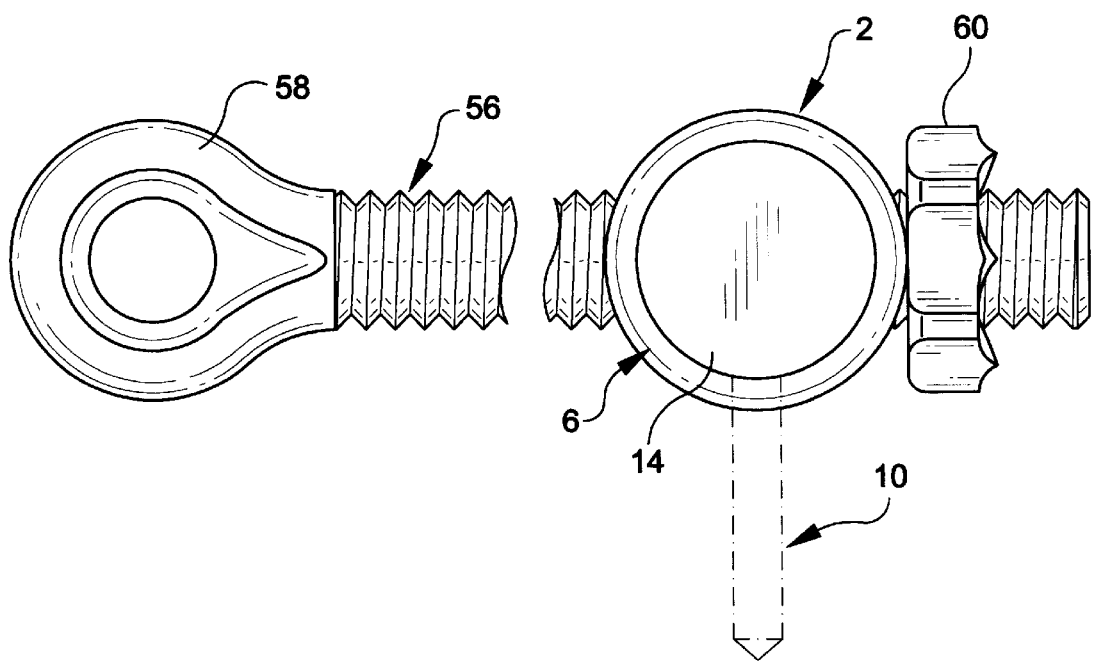
FIG. 2 shows the connecting element of FIG. 1 seen in direction of the arrow A, whereby the lower part of the pedicle screw 10 of FIG. 1 is shown in phantom and additionally a rod 56 is shown.

The tension member 4 comprises a first section 12 for receiving the pedicle screw 10 and a second section 14 for receiving and fixing a rod (not shown) by clamping for stabilizing a human spine. The first section 12 is a threaded shank onto which the nut 8 can be screwed. The second section 14 attaches to the shank 12 via a curved transition region 16 and has larger transverse dimensions than the shank 12. As can be seen in FIG. 2, the second section 14 has a cylindrical shape. The second section 14 includes a circular through-receiving opening 18 (shown in FIG. 1) which extends transversely relative to the longitudinal axis 20 of the connecting member 2.

The sleeve 6 is also cylindrical. The sleeve 6 includes a through-opening 28 for the shank 12 in an end plane 26 facing the shank. Teeth 30 are formed around the through-opening 28. The cylindrical inner wall surface 34 of the sleeve 6 nearly matchingly, however, glidingly receives the cylindrical outer wall surface 36 of the second section 14. The sleeve wall 32 includes a conical ring surface 38 which is inclined towards the opening 30 and which is parallel to the surface area 40 of the transition region 16 of the first section 14. In the sleeve walls 32 two circular through-openings 42 located opposite each other are formed which (in the position of the sleeve 6 shown in FIG. 1), are concentric with the opening 18 of the tension member but which have a slightly smaller diameter.

The nut 8 includes an essentially hexagonal head 44 which is adjoined by a collar 46 towards the shank, whereby the nut 8 engages with the collar 46 with a circular opening 50 in the head 52 of the pedicle screw 10.

On its outer surface the head 52 of the pedicle screw 10 includes teeth 54 around the opening 50 in order to engage with teeth 30 of the sleeve 6.

The connecting element 2 is used as follows. At first it is passed with the shank 12 through the opening 50 of the pedicle screw head 52. Thereafter, the nut 8 is screwed onto the shank 12 so far until the opening 18 of the tension member 4 and the openings 42 of the sleeve 6 are concentric. Then, the rod to be secured (not shown in FIG. 1 but shown in FIG. 2) is passed through the openings and the nut 8 is tightened so that the sleeve 6 is fixed against the head 52 of the pedicle screw 10 and simultaneously the sleeve is displaced towards the shank 12 relative to the tension member 4 so far until the rod (between the openings 18 and 42) is clamped.

FIG. 2 shows the connecting element 2 of FIG. 1 in direction of the arrow A. Therein, the pedicle screw 10 is shown with phantom lines. Additionally, a threaded rod 56 fixed in the connecting element 2 for stabilizing a spine is shown. At an end, the rod 56 has an eye-shaped opening 58 for securing the rod at an iliac screw. The rod 56 is passed transversely (preferably perpendicular) relative to the longitudinal direction 20 of the connecting element 2, through the openings 42 of the sleeve 6 and through the opening 18 of the second section. A nut 60 is screwed on at the end of the rod 56 opposite the end having the opening 58. The nut 60 is screwed against the connecting element 2. As a result, a traction can be applied to the rod 56 and thus to the screw passed through the opening 58 before the rod 56 is fixed in the connecting element 2.

Figure 3:
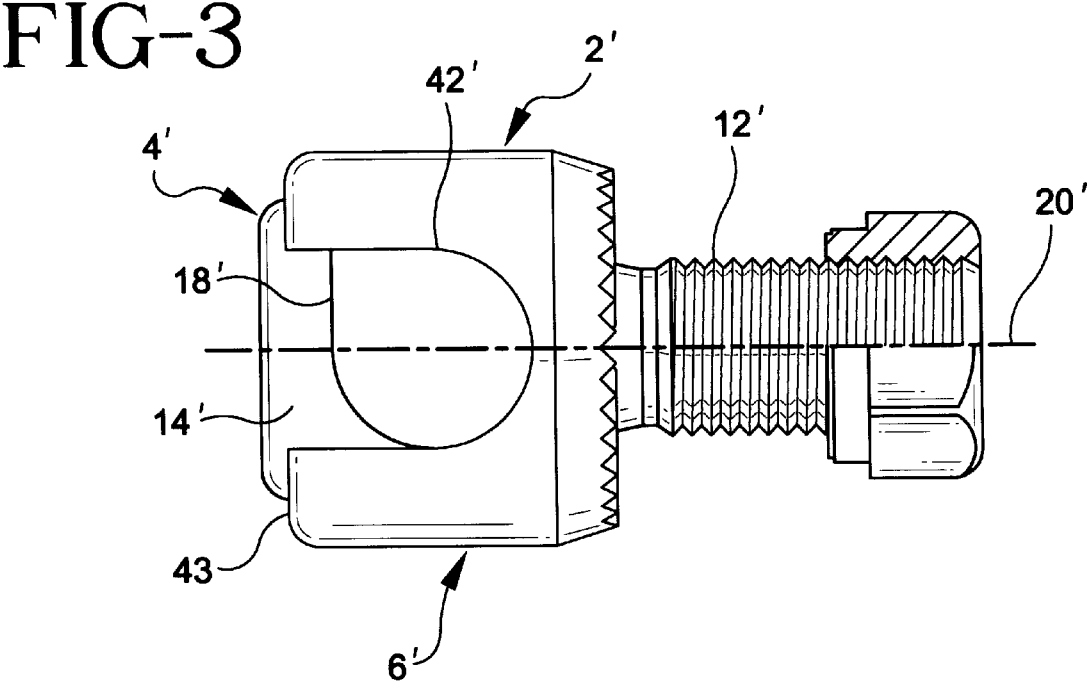
FIG. 3 shows a second embodiment of the connecting element 2' according to the invention in elevational view and partly in sectional view.
Figure 4:
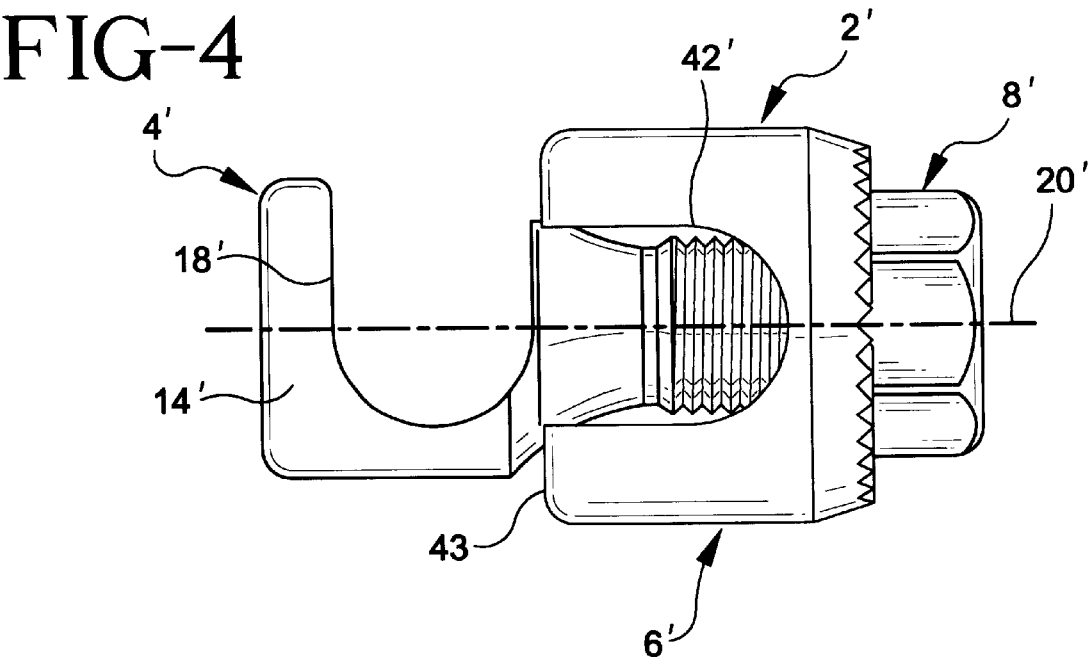
FIG. 4 shows the connecting element of FIG. 3, whereby the sleeve 6 has been slidingly displaced and is located in a position which allows for putting the rod into the connecting element 2.
Figure 5:
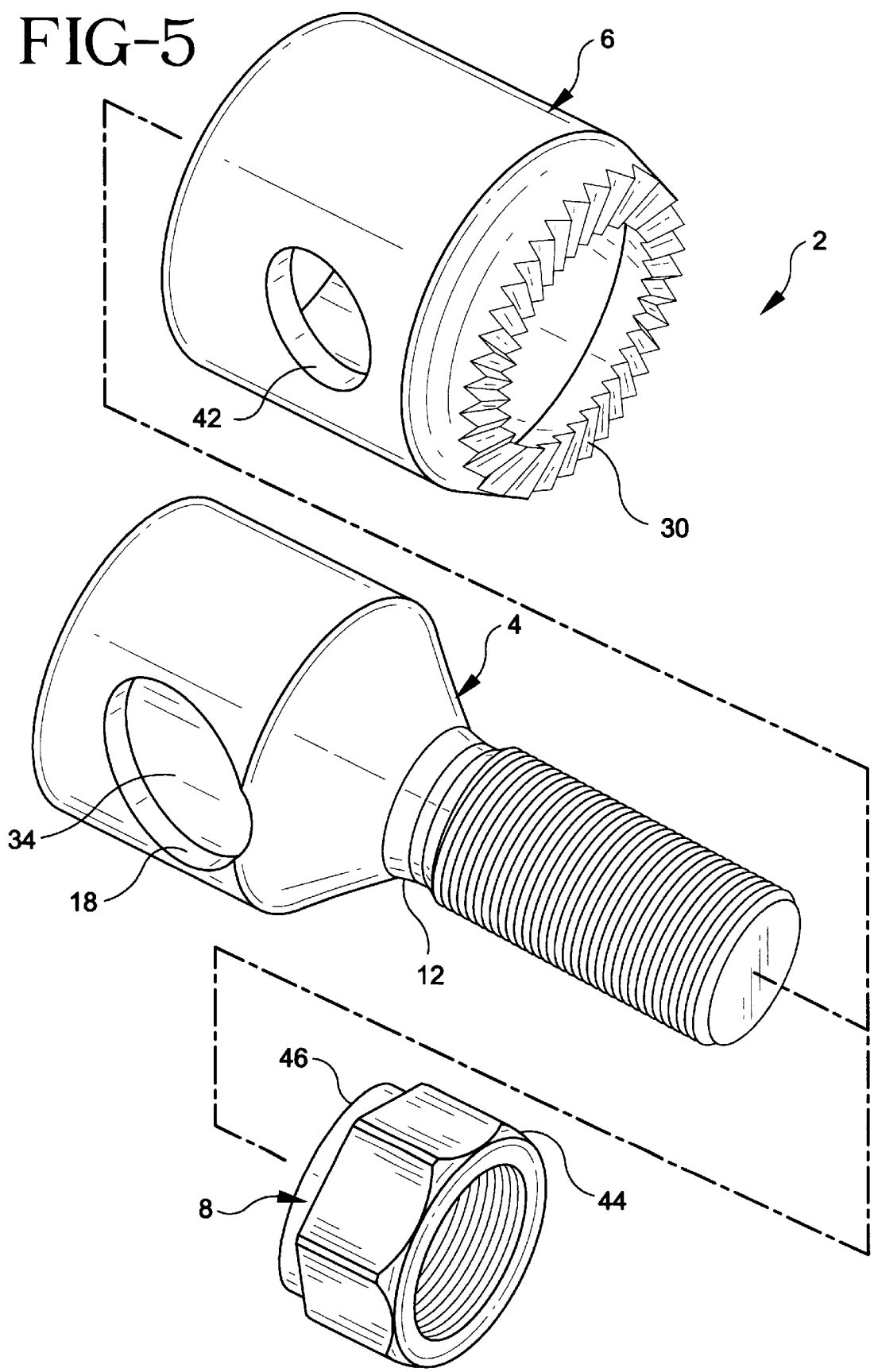
FIG. 5 shows an exploded isometric view of connecting element of FIG. 1.
Figure 6:
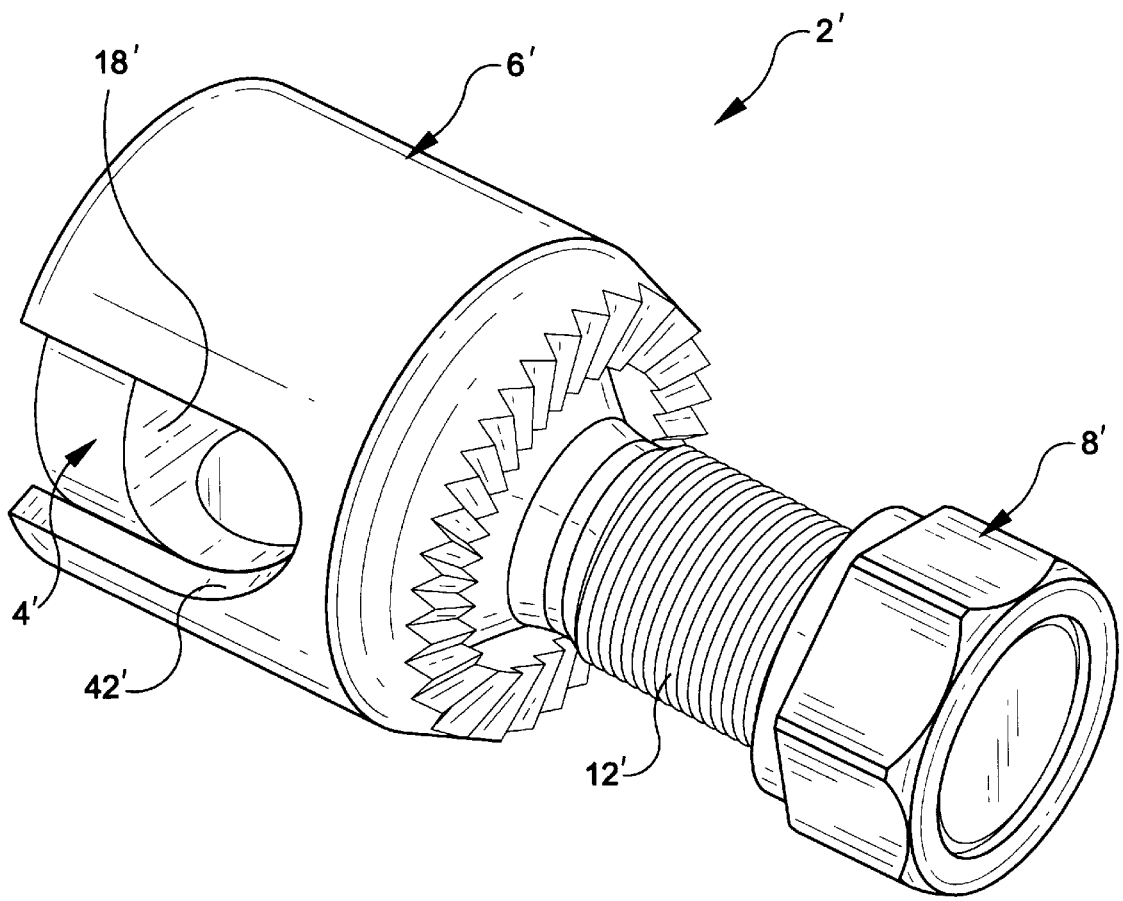
FIG. 6 shows an isometric view of the connecting element of FIG. 1.

The FIGS. 3 and 4 show a second embodiment 2' of the connecting element according to the invention. The connecting element 2' differs from the connecting element 2 shown in FIG. 1 essentially in that instead of the opening 18 of the connecting element 2, the connecting element 2' is provided with a recess 18'; and further instead of the openings 42, the connecting element 2' is provided with recesses 42'.

The recess 18' is located in a second section 14' of a tension member 4' and is open transversely relative to an axis 20' of a threaded shank 12' (see FIG. 4). Apart from the open side, the recess 18' is formed like an elongated hole which is oriented perpendicular relative to the longitudinal axis 20'.

The recesses 42' are provided in a sleeve 6' and have a shape which is essentially the same as that of the recess 18', however, they are open towards the end 43 of the sleeve 6' opposite the shank 12', whereby the longitudinal axes of the recesses 42' are parallel relative to the shank axis 20'.

In FIG. 3 the sleeve 6' is slid over the second section 14' such that an enclosure for a rod is provided by superposition of the recesses 18' and 42'. In FIG. 4 the sleeve 6' is shown displaced towards the shank 12' so that the recess 18' of the tension member 4' is not covered and a rod can be put into the recess 18' through its open end. Subsequently, the rod can be fixed by clamping as the sleeve 6' is slid toward the second section 14' and the nut 8' is tightened as explained above.

We claim:

1. A connection element (2) for fixing a rod (56) at a pedicle screw (10) in a stabilizing system for a human spine, said connecting element comprising:
   (a) a tension member (4) comprising:
      (1) a first section comprising a threaded shank (12) for extending on one side of a pedicle screw head (52) for receiving and clamping said pedicle screw;
      (2) a second section (14) for extending on an opposite side of said screw for receiving and clamping said rod (56), when said rod (56) is passed through an opening in said second section (14) an inclined transition surface extending between said first and second sections;
   (b) a sleeve (6) slidingly arranged on said second section (14), said sleeve (6) having an opening (28) for said threaded shank (12) and said sleeve (6) having two openings (42) for said rod (56), said sleeve having an inclined surface complimentary to said inclined transition surface; and
   (c) a nut (8) for being screwed onto said threaded shank (12) against said one side of said screw for fixing said sleeve against said opposite side of said head of said pedicle screw (10) and simultaneously for fixing said rod within said connecting element (2) when said opening (18) and said two openings (42) are concentric when said sleeve (6) is slid into an appropriate position with respect to said second section (14).

2. A connecting element according to claim 1, wherein the nut (8, 8') comprises a collar (46) for engagement with an opening (50) of the pedicle screw head (52).

3. A connecting element according to claim 1, wherein said sleeve (6) comprises teeth (30) located around the opening (28) for the shank (12) for engagement with teeth (54) of the pedicle screw head (52).

4. A connecting element according to claim 3, wherein said sleeve (6) is round in cross-section.

5. A connecting element according to claim 4, wherein said opening (28) of said sleeve (6) for the shank (12) has a cross section smaller than the cross section of said second section (14).

6. A connecting element for fixing a rod at a pedicle screw in a stabilizing system for the human spine, comprising a connecting element having a first section for receiving a pedicle screw having a head with an aperture through which said first section extends and a second section for extending on one side of said aperture for receiving and clamping said rod when said rod is passed through a hole in said second section, wherein said second section is formed as a tension member and said first section having a threaded shank, an inclined transition surface extending between said first section and said second section; a tubular sleeve is slidingly arranged on said second section, said sleeve having an opening for receiving said threaded shank and two openings located opposite each other in a sleeve wall for positioning the rod, said sleeve having an inclined surface complimentary to said inclined transition surface on said connecting element and a nut for being screwed onto the threaded shank and into contact with a side of said pedicle screw opposite said second section in order to fix the sleeve at said head of the pedicle screw and simultaneously clamping said rod between said sleeve and second section.

7. A connecting element according to claim 6, wherein the hole of the second section is circular for receiving said rod (56).

8. A connecting element according to claim 6, wherein the sleeve (6, 6') comprises teeth (30) around the opening (28) for the shank (12, 12') for engagement with teeth (54) of the pedicle screw head (52).

9. A connecting element according to claim 8, wherein the sleeve (6, 6') is round in cross-section.

10. A connecting element according to claim 9, wherein a cross section of said opening (28) of the sleeve (6, 6') for the shank (12, 12') is smaller than a cross section of the second section (14, 14').

11. A connecting element according to claim 6, wherein said nut (8) comprises a collar (46) for engagement with an opening (50) of said pedicle screw head (52).

\* \* \* \* \*